United States Patent [19]
Matoushek

[11] Patent Number: 5,439,871
[45] Date of Patent: Aug. 8, 1995

[54] METHOD FOR DETECTING UNUSABLE DONOR IN A DYE DONOR WEB

[75] Inventor: Robert J. Matoushek, Rochester, N.Y.

[73] Assignee: Eastman Kodak Company, Rochester, N.Y.

[21] Appl. No.: 236,783

[22] Filed: Apr. 29, 1994

Related U.S. Application Data

[63] Continuation of Ser. No. 895,748, Jun. 9, 1992, abandoned.

[51] Int. Cl.$^6$ .................. B41M 5/035; B41M 5/38; G01N 21/00
[52] U.S. Cl. .................. 503/227; 356/239; 428/195; 428/913; 428/914
[58] Field of Search .................. 428/195, 913, 914; 503/227; 356/237, 239, 432

[56] References Cited

U.S. PATENT DOCUMENTS 4,588,329 12/1985 Honda .................. 346/76 PH

Primary Examiner—B. Hamilton Hess
Attorney, Agent, or Firm—Milton S. Sales

[57] ABSTRACT

A method and apparatus for detecting defects in a dye donor web having repeating series of patch colors. If defective regions in a dye donor web are found during manufacture, an opaque mark is physically placed on a color patch of the repeating series in which the defect occurs. As the dye donor web is advanced, two beams of light of a color to which the color patch is transmittable impinge on the dye donor web. The beams are in substantial alignment in a direction transverse to the web path and are positioned such that the mark (if present) aligns with one of the two light beams and not the other beam. By sampling the transmission or non-transmission of the two light beams through the dye donor web, a signal can be generated whenever the simultaneous non-transmission of the one light beam and transmission of the other light beam is detected.

8 Claims, 1 Drawing Sheet

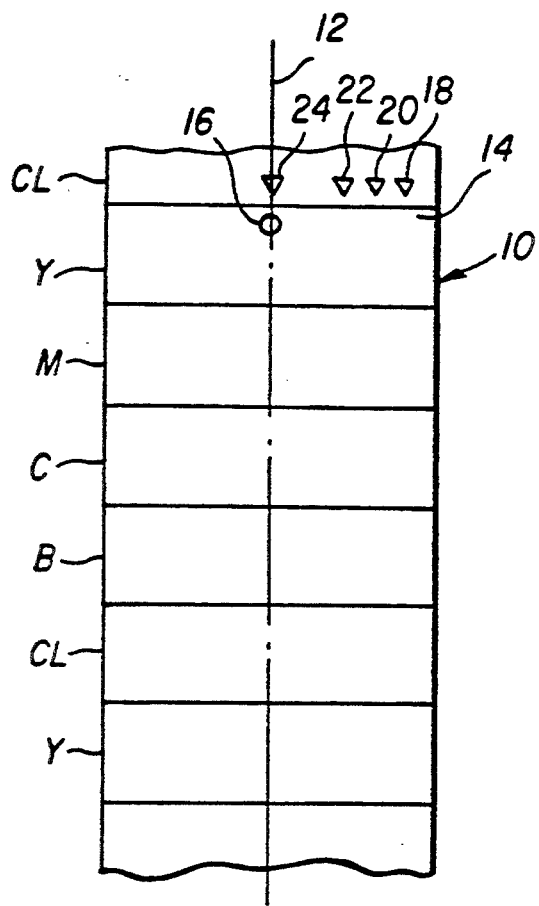
FIG. 1
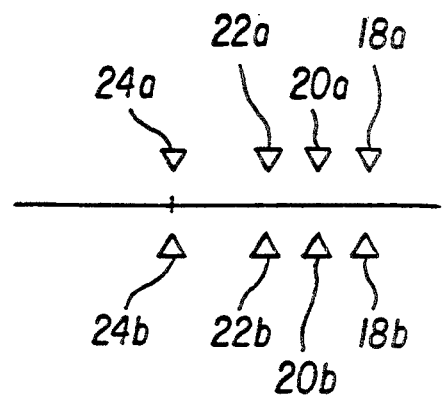
FIG. 2
| DONOR | LED | | |
|---|---|---|---|
| | BLUE | GREEN | RED |
| YELLOW | 0 | 1 | 1 |
| MAGENTA | 0 | 0 | 1 |
| CYAN | 1 | 0 | 0 |
| BLACK | 0 | 0 | 0 |
| CLEAR | 1 | 1 | 1 |
FIG. 3

METHOD FOR DETECTING UNUSABLE DONOR IN A DYE DONOR WEB

CROSS-REFERENCE TO RELATED APPLICATION

This is a continuation of U.S. patent application Ser. No. 07/895,748 filed in the name of Robert J. Matoushek on Jun. 9, 1992, now abandoned.

TECHNICAL FIELD OF THE INVENTION

The present invention generally relates to thermal printing, and, more particularly, to detecting unusable portions of a dye donor web.

BACKGROUND OF THE INVENTION

The thermal printing process is conducted by selectively heating pixel-sized areas within a color patch of a dye donor web until the dye melts or vaporizes and is transferred to a dye receiver where it is deposited and solidified. The quantity of dye transferred and the resulting print density is determined by many factors including the amount of dye on the donor material. Conversely, a variation in print density can be caused by irregularities in the dye layer of the donor material. The state of manufacturing technology today is such that the dye coated donor material is occasionally defective or has defective patches. Defective donor material within a color patch will produce a defective print which requires remaking. Using defective donor wastes both time and receiver material.

If the location of defective color patches along the donor web could be marked, when a mark signifying a defective color patch is sensed during printing, the defective color patch, or a series of color patches containing the defective one could be passed over in the printing process. This would eliminate defective prints, speed the printing process, and decrease wasted receiver material. Accordingly, it will be appreciated that it would be highly desirable to identify the defective areas in the donor web during manufacturing and to detect the marked area during printing so that defective areas can be bypassed.

SUMMARY OF THE INVENTION

The present invention is directed to overcoming one or more of the problems set forth above. More particularly, if defective regions are found during donor web manufacture, an opaque mark is physically placed on a color patch of the repeating series in which the defect occurs. The present invention relates to a method and apparatus for using the opaque mark to identify defective regions of a dye donor web so that they can be skipped during printing operations.

The present invention provides for detecting defects in a dye donor web having repeating series of at least two dye donor patch colors wherein light of a predetermined color is transmittable through at least one of the dye donor patches of each repeating series of patches. The present invention includes providing a mark on one of the dye donor patches of a repeating series of patches which has at least one defect in the series. The mark being opaque to light of the predetermined color, and the one of the dye donor patches being transmittable to light of the predetermined color. As the dye donor web is advanced along a path adjacent a source of light of the predetermined color, two beams of light of the predetermined color impinge on the dye donor web. The beams are in substantial alignment in a direction transverse to the web path and are positioned such that the mark (if present) aligns with one of the two light beams and not the other beam. By sampling the transmission or non-transmission of the two light beams through the dye donor web, a signal can be generated whenever the simultaneous non-transmission of the one light beam and transmission of the other light beam is detected. Since this state of transmission occurs only when a mark is present, the signal can be used to indicate the presence of a defective region within the series.

Other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 1 is a diagram of a dye donor web in the presence of detectors for detecting dye patch colors and the presence of marks on the donor.

FIG. 2 is an end view of the donor and detectors of FIG. 1 illustrating the placement of the detectors.

FIG. 3 is a logic table indicating the signals from the detectors for the color patches on the donor web.

DETAILED DESCRIPTION OF THE PREFERRED EMBODIMENTS

In an embodiment as illustrated in FIGS. 1-3, a dye donor web 10 has a centerline 12 and a repeating series of at least two differently colored dye donor patches. As shown in FIG. 1, the repeating series preferably includes yellow (Y), magenta (M), and cyan (C) dye donor patches with the yellow patch being the leading first patch and having a leading edge 14. The first patch has been tagged, such as during manufacture, with an opaque mark 16, preferably near leading edge 14 and/or along centerline 12 designating that a defect has been detected in the patch series.

The printer includes a plurality of detectors 18, 20, 22, and 24. Referring to FIG. 2, each detector includes a light source 18a, 20a, 22a, and 24a of a specific color (red, green, blue, and red, respectively) and an associated light sensor 18b, 20b, 22b, and 24b. The light sources may be LED's. Detector 24 is located along the centerline 12 of the path of web 10. As illustrated in FIG. 1, if an opaque mark is placed on the patch to denote that there is a defect in the series, it will align with detector 24 but not align with detectors 18, 20, and 22.

As illustrated by the table of FIG. 3, the yellow patch transmits red and green light and blocks blue light, while the magenta patch transmits red light and blocks both blue and green light. The cyan patch transmits only blue light and blocks both green and red light. A clear patch transmits all three colors while a black patch or opaque mark blocks all three colors of light. (As is commonly used in the art, the logic tables use "1" to indicate transmission and "0" to indicate non-transmission.) Therefore, depending on the color of the light source and the color of the patch, there will be either transmission or non-transmission of the light through the patch. These different light transmission characteristics of the colored patches can provide a means for determining the color of the patch advancing adjacent the detectors. Note that the table shown in FIG. 3 may depart from conventional theory known to those skilled in the art because the materials of the illustrated embodiment may not be pure colors. When advancing dye donor web 10 adjacent detectors 18, 20, 22, and 24, the different light transmission characteristics of the dye donor patches can be sampled.

When an opaque mark is present, indicating defective regions, the selected series containing the defective regions will be bypassed. In a preferred embodiment of the present invention, the first dye donor patch is yellow. Two light sources 24a and 18a, both of red light, are positioned to emit two beams of red light onto dye donor web 10. Referring to FIG. 3, the yellow patch is transmittable by red light, while opaque mark 16 placed on a portion of the yellow patch causes that portion of the yellow patch to not be transmittable by red light. As shown in FIG. 1, detector 24 aligns with the placement of opaque mark 16, while detector 18 does not. As dye donor web 10 advances adjacent detectors 24 and 18, the detectors can be continuously sampled. Accordingly, when the section of the yellow patch marked with the opaque mark advances past the detectors, the sampling of detector 24 indicates non-transmission while the sampling of detector 18 indicates transmission. These differing responses of the detectors indicate the presence of the opaque mark. A signal can be generated to cause the repeating series containing the defective regions to be bypassed.

In contrast, when an opaque mark is not present, the samplings of detectors 24,18 will not differ. For example, in the embodiment wherein the patch is yellow and the two light sources 24a and 18a emit red light, when the yellow patch advances past the detectors the sampling of detector 24 indicates transmission and the sampling of detector 18 also indicates transmission. Since both detectors indicate transmission, the responses are the same. If no mark is detected in the entire selected series, it can be assumed that there are no defective regions in that selected series.

Operation of the present invention is believed to be apparent from the foregoing description, but a few words will be added for emphasis. Detection of the opaque mark can be done by conventional color patch detectors. The normal system used to detect individual patches of yellow, magenta, cyan, black, or clear donor consists of a red, a green and a blue LED used in combination in the transmitting mode. For example, in a preferred embodiment, a red LED at the donor centerline indicates zero transmission when reading the opaque mark, while the regular red LED will indicate high transmission in the normal yellow patch. This difference in the samplings from the two LEDs indicates that the donor at the centerline has been altered, signifying defective donor. In contrast, if both red LEDs indicate high transmission. the signals from the two LEDs are not different, signifying no defective donor.

While the invention has been described with particular reference to the preferred embodiments, it will be understood by those skilled in the art that various changes may be made and equivalents may be substituted for elements of the preferred embodiment without departing from invention. For example, defective donor could be tagged or marked as it passes through the slitting operation prior to final spooling during manufacture. An ink jet printer could be used to add a black mark on the centerline of the donor near the leading edge of each yellow patch of defective donor. In addition, many modifications may be made to adapt a particular situation and material to a teaching of the invention without departing from the essential teachings of the present invention.

It can now be appreciated that there has been presented a method for detecting and bypassing unusable donor in a dye donor web having a repeating series of patches.

As is evident from the foregoing description, certain aspects of the invention are not limited to the particular details of the examples illustrated, and it is therefore contemplated that other modifications and applications will occur to those skilled in the art. For example, the invention detects black marks on the color patches as well as voids. It is accordingly intended that the claims shall cover all such modifications and applications as do not depart from the true spirit and scope of the invention.

What is claimed is:

1. A method for detecting defects in a dye donor web having repeating series of at least two dye donor patch colors wherein light of a predetermined color is transmittable through at least one dye donor patch of each repeating series of patches, said method comprising the steps of:

providing a mark on one of the dye donor patches of a repeating series of patches which has at least one defect in the series, said mark being opaque to light of said predetermined color, said one of the dye donor patches being transmittable to light of said predetermined color;

advancing the dye donor web along a path adjacent a source of light of said predetermined color such that two beams of light of said predetermined color impinge on the dye donor web, said beams being in substantial alignment on the web in a direction transverse to the path such that the mark aligns with one of said two light beams and not the other;

sampling the transmission or non-transmission of the two light beams through the dye donor web; and generating an error signal, indicative of the presence of a mark in the series of dye donor patches, upon detecting the simultaneous non-transmission of the one light beam and transmission of the other light beam.

2. A method, as set forth in claim 1, wherein said dye donor web has a longitudinal centerline and said mark is provided proximate said centerline.

3. A method, as set forth in claim 1, wherein each repeating series of patch colors of said dye donor web has a leading edge and said mark is provided proximate said leading edge.

4. A method, as set forth in claim 1, wherein said one of the dye donor patches is the first patch of the repeating series.

5. For use in a thermal printing apparatus having a light source of a predetermined color emitting two beams of light onto a dye donor media advancing along a path adjacent said source of light in a direction traverse to the path, dye donor media comprising:

a repeating series of at least two dye donor patch colors wherein light of a predetermined color is transmittable through at least one dye donor patch of each repeating series of patches; and a mark provided on one of the dye donor patches of a repeating series of patches which has at least one defect in the series, said mark being opaque to light of said predetermined color and being positioned to align with one of two light beams and not the other, said one of the dye donor patches being transmittable to light of said predetermined color.

6. The dye donor media as defined by claim 5 wherein said dye donor web has a longitudinal centerline and said mark is provided proximate said centerline.

7. The dye donor media as defined by claim 5 wherein each repeating series of patch colors of said dye donor web has a leading edge and said mark is provided proximate said leading edge.

8. A dye donor media, as set forth in claim 5 wherein said one of the dye donor patches is the first patch of the repeating series.

* * * * *